United States Patent
Craggs

(10) Patent No.: US 8,644,938 B2
(45) Date of Patent: Feb. 4, 2014

(54) NEUROMODULATION DEVICE FOR PELVIC DYSFUNCTION

(75) Inventor: Michael Craggs, London (GB)

(73) Assignee: Nephro-Urology Clinical Trials Limited (GB)

( * ) Notice: Subject to any disclaimer, the term of this patent is extended or adjusted under 35 U.S.C. 154(b) by 1088 days.

(21) Appl. No.: 12/281,691

(22) PCT Filed: Mar. 6, 2007

(86) PCT No.: PCT/EP2007/052106
§ 371 (c)(1),
(2), (4) Date: Jan. 2, 2009

(87) PCT Pub. No.: WO2007/101861
PCT Pub. Date: Sep. 13, 2007

(65) Prior Publication Data
US 2009/0222058 A1 Sep. 3, 2009

(30) Foreign Application Priority Data
Mar. 6, 2006 (GB) .................................. 0604483.8

(51) Int. Cl.
*A61N 1/00* (2006.01)
(52) U.S. Cl.
USPC ............................................. 607/41; 607/138
(58) Field of Classification Search
USPC ..................................... 607/138, 2, 39–41, 62
See application file for complete search history.

(56) References Cited

U.S. PATENT DOCUMENTS 4,909,263 A * 3/1990 Norris .............................. 607/39
5,702,428 A 12/1997 Tippey et al.

(Continued)

FOREIGN PATENT DOCUMENTS

| DE | 4022074 A1 | 2/1992 |
| WO | 90/12617 A | 11/1990 |
| WO | 02/17987 A | 3/2002 |
| WO | 2004/067085 A | 8/2004 |

OTHER PUBLICATIONS

International Search Report for PCT/EP2007/052106, dated May 29, 2007, mailed Jun. 5, 2007.

(Continued)

*Primary Examiner* — Christopher D Koharski
*Assistant Examiner* — Catherine Voorhees
(74) *Attorney, Agent, or Firm* — Banner & Witcoff, Ltd.

(57) ABSTRACT

A wearable neuromodulation device (1), configured for insertion into a pelvic orifice of the human body for treating urinary incontinence, faecal incontinence, muscle wastage, spasm and/or spasticity by applying electrical stimulation signals to pudendal nerves through the wall of the rectum or vagina, comprises at least one sensor, such as an electromyographic (EMG) sensor (11) or pressure sensor (12, 13), configured to detect conditions that indicate a requirement for stimulation. The device (1) is autonomous but may be arranged to communicate with an external device (28) comprising an alarm (33), to alert a user to their condition, and/or means (34) for allowing the user to control the stimulation applied by the device. Alternatively, or additionally, the device (1) may communicate with a computer (37) to store patient data for review by a medical professional and/or permit updating of device software. The device (1) may communicate with the external device(s) (28, 37) via wired or wireless links, including Bluetooth or a Body Area Network (BAN). Such a device (1) may comprise an outer sleeve (5) that can be replaced in event of damage, deterioration or discolouration.

27 Claims, 11 Drawing Sheets

(56) References Cited

U.S. PATENT DOCUMENTS

| | | | |
|---|---|---|---|
| 2003/0100932 A1* | 5/2003 | Ciaff | 607/48 |
| 2006/0036188 A1* | 2/2006 | Hoffman et al. | 600/591 |
| 2006/0122678 A1* | 6/2006 | Olsen et al. | 607/117 |
| 2006/0190048 A1* | 8/2006 | Gerber | 607/41 |
| 2007/0027495 A1* | 2/2007 | Gerber | 607/41 |
| 2007/0112403 A1* | 5/2007 | Moffitt et al. | 607/116 |

OTHER PUBLICATIONS

International Preliminary Report on Patentability Regarding PCT/EP2007/052106 (Issued on Sep. 9, 2008), 7 pages.

* cited by examiner

NEUROMODULATION DEVICE FOR PELVIC DYSFUNCTION

FEILD

The invention relates to a neuromodulation device and method that is suitable for controlling pelvic dysfunction, including conditions such as urinary incontinence, faecal incontinence and muscle wastage.

BACKGROUND

Urinary incontinence, in other words, the involuntary leakage of urine, affects up to twenty percent of the population across all ages. Incontinence can be divided into categories. Urge incontinence describes a condition where a person has a sudden need to pass water is unable to prevent bladder contraction and, thus, urine leakage, until they can reach a toilet. This condition can be associated with an unstable or overactive bladder. Stress incontinence is a condition where urine is leaked in response to sudden pressure on the bladder that the sphincter cannot withstand. For instance, urine leakage may occur in response when laughing, coughing or from sudden movements such as jumping. This condition is often associated with an incompetent striated urethral sphincter. Also, a person may suffer from a combination of urge incontinence and stress incontinence, known as mixed incontinence.

Incontinence can arise from a number of possible causes, including conditions associated with child birth injuries, that weaken the urethral sphincter and/or pelvic floor muscles, prostate surgery, disease and idiopathic problems. In patients who have suffered a spinal trauma, the nerves and reflexes controlling the bladder may be affected, leading to incontinence.

Normally, the sphincter is controlled from the central nervous system, via the pudendal nerves. These nerves, which originate in the sacral spinal cord, course through the sacral nerve roots and then on to the pelvic floor and sphincter. En route, the pudendal nerves pass close to the rectum and comprise a motor and sensory division. Activity in the pudendal sensory nerves, together with descending signals from the brain, help to prevent the bladder contracting involuntarily while it is filling, by means of inhibitory pathways in the spinal cord. The bladder and sphincters are normally coordinated by the brain stem and, when the bladder is full, it is these pathways, together with social and cognitive factors, that determine when the conditions are right for micturition.

In addition, other mechanisms normally act to prevent involuntary leakage of urine. During coughing, straining or other actions causing pressure in the abdomen, both the urethral and anal sphincters contract reflexly to prevent incontinence. Furthermore, the tone of the urethral and anal sphincters increase automatically as the bladder fills, to prevent leakage. This is known as the "guarding reflex".

For some years, methods involving electrical stimulation of the sacral nerves have been used to help prevent incontinence. The stimulation of one neural pathway to control the activity in another neural pathway is commonly known as neuromodulation. The stimulation may be excitatory or inhibitory. A review of some of these techniques is given by Craggs M. D. in "Textbook of the Neurogenic Bladder, Adults & Children", Corcos J. & Schick E. (eds.), 2004, London: Martin Dunitz, pp 625-635. At low levels of stimulation, an overactive bladder can be controlled via spinal cord inhibitory pathways. At higher levels of stimulation, the sphincter muscle is also brought into direct action via its pudendal motor nerves. These techniques can be combined to provide a therapy for controlling urinary incontinence.

Previously, neuromodulation has been effected with devices comprising stimulating electrodes for placement at various positions, for example, in the anal canal, vagina or skin sites in the region of the pudenda, such as the dorsal penis, dorsal clitoris or perineum. In all these positions, it is possible to activate sacral reflexes by continuously stimulating different branches of the sensory pudendal nerves, which are able to suppress or inhibit an overactive bladder.

More recently, implanted devices have been developed that can reproduce these benefits by applying continuous stimulation through electrodes placed at various sites along the route of the pudendal nerves to the sacral spinal cord. The most common site for such implanted electrodes has been the point at which the sacral nerve roots leave the spinal cord through the sacral foramina.

Such devices suffer from the drawback that the stimulation provided may become ineffective through habituation, following continuous stimulation of the spinal pathways. This problem has been addressed by providing conditional stimulation devices. US 2005/0113881 A1 discloses a prior implanted device arranged to provide stimulation in response to certain conditions. The device includes a sensor that detects motion of or pressure in the bladder via signals conveyed by the muscles of a patient. If the output of the sensor suggests that there is a likelihood of involuntary urine flow, the device stimulates the muscles to inhibit urine flow. Another prior implanted device is disclosed in U.S. Pat. No. 6,836,684, and is arranged to provide conditional stimulation to the nerves of a patient based on events detected via nerve signals.

For many patients, an implant is often inappropriate. The implantation of a stimulator device is a surgical procedure and is thus associated with a degree of risk. Furthermore, an implanted device cannot be serviced or removed easily as this would require further surgical intervention. Such devices are sometimes also unsuitable for treatment of children, due to their rapid growth. However, there are also drawbacks associated with non-implanted devices, as they may be uncomfortable, unsuitable for prolonged treatment sessions or difficult to insert and remove.

Thus, both implanted and non-implanted devices have drawbacks that increase the probability that a patient will abandon their therapy in favour of other methods of treatment. However, the available alternative treatments, such as drugs and incontinence pads have their own disadvantages, such as side-effects, lack of comfort or convenience and social stigma.

BREIF SUMMARY

According to a first aspect of the invention, a wearable neuromodulation device, configured to be insertable into a pelvic orifice of a human body, comprises a plurality of electrodes configured to apply focussed electrical stimulation signals to the pudendal nerves through the wall of a rectum or vagina of the human body, at least one sensor configured to detect one or more conditions within said human body that indicate a requirement for stimulation and means for applying an electrical signal to said electrodes selectively, in response to a determination that said stimulation is required based on a detection of said one or more conditions.

The term "wearable" means that the device is suitable for continual wear. In other words, a patient using the device would be free to move and continue everyday activities, such as walking, sitting and standing, without discomfort.

The device can thus provide stimulation to the pudendal nerves of a patient as and when required to inhibit bladder activity, bowel activity, spasm and/or spasticity and to activate the sphincters to prevent incontinence. The stimulation can be triggered automatically, based on detected signals associated with a muscle contraction, for example, arising from bladder sphincter dyssynergia, guarding reflexes or a voluntary contraction. As stimulation is provided only when required, the disadvantages of habituation associated with prior continuous stimulation devices are avoided. In addition, the power consumption of the device over a given period of time is decreased, potentially reducing the need for recharging and/or changes of batteries and thus increasing convenience to the patient.

As the device is a wearable device, it is minimally invasive and easily removable. It can be deployed and maintained without surgery, resulting in an improved ease of use. Furthermore, the device can be formed from a material, such as soft or spongy silicone rubber, that can be suitably profiled so that it can be worn comfortably by a patient. The provision of such a highly wearable, comfortable device, can promote patient compliance.

The device can be used to assess or intervene in a variety of conditions, by enabling the control of urinary incontinence and faecal incontinence, spasticity of the lower limbs, improvement of bladder and bowel capacity, training reflexes and/or promoting tissue viability. The device may also be used as an early intervention tool, to prevent the deterioration of muscles after paralysis.

The device may comprise a module comprising a plurality of electrical contacts, means for applying an electrical signal to the electrical contacts and a removable outer sleeve comprising the plurality of electrodes, configured so that when the sleeve is positioned over the module, the electrodes are connected to corresponding ones of the electrical contacts. Such a sleeve can be replaced in the event of damage, deterioration or discolouration, potentially improving patient compliance and reducing the need to replace the device. This, in turn, may lower wastage of devices and the costs associated with providing such therapy. The electrical contacts may be elongated along a longitudinal axis of the device, to accommodate a variety of sleeves in which the electrodes are located at different positions.

The at least one sensor may comprise a pressure sensor for detecting pressure in the vicinity of the device, wherein said determination ascertains whether the detected pressure exceeds a predetermined threshold, and/or a sensor for detecting electromyographic (EMG) signals in a sphincter muscle, wherein said determination ascertains whether the electromyographic signals indicate inappropriate muscle activity. In this case, the device may comprise means for determining whether a frequency of detections of one or more conditions requiring stimulation exceeds a predetermined threshold and, in response to a positive determination, applying continuous stimulation for an extended time period.

The electrodes may be formed of carbon loaded silicone rubber. Carbon loaded silicone rubber is flexible, to reduce any discomfort from wearing the device, and has good potential biocompatibility with the mucosa and skin of a user. Other suitable electrode materials include stainless steel, platinum and other noble metals.

The plurality of electrodes may comprise a tripole arrangement. The tripole arrangement may be an unbalanced tripole arrangement, wherein a first one of said plurality of electrodes is larger than, and is of opposite charge to, second and third ones of said plurality of electrodes. Such an arrangement permits the stimulation signals to be focussed in the region of the pudendal nerves. Said second and third electrodes may be positioned with an angle of 100 to 140 degrees therebetween, with respect to a longitudinal axis of the device, said first electrode being positioned between said first and second electrodes, within said angle.

The device may comprise a first formation, configured to limit the insertion of the device into said pelvic orifice, and a second formation configured to retain said plurality of electrodes in a rectum. The first and second formations may be configured to retain said plurality of electrodes at a distance of at least 3 centimetres from the external meatus of the anal canal. The device may be configured so that the distance between the first and second formations is adjustable.

Such a device may comprise a transmitter configured to transmit data relating to an output of the at least one sensor to an external device.

The device may comprise a receiver arranged to receive from a remote device program instructions to be executed by the means for applying electrical stimulation signals.

The invention also provides a neuromodulation arrangement comprising the wearable modulation device and an external device, where the wearable device is configured to transmit data relating to the output of the at least one sensor of the at least one sensor to the external device.

The external device may be arranged to generate an alert in response to data transmitted from the neuromodulation device, to inform a user of their condition. For example, the external device may comprise a vibration means to provide a discreet vibrating alert, a visual alert means and/or an audible alert means. In this manner, a patient can be alerted of an imminent need to empty their bladder or rectum. The external device may comprise control means arranged to allow a user to control the application of the electrical stimulation signals by said electrodes.

Where provided, the associated device may comprise control means permitting a user to control the stimulation applied by the electrodes. In this manner, a patient can override the conditional stimulation applied by the device to provide continuous stimulation or to permit voiding of their bladder or bowel.

The connection between the device and associated device may be in the form of a wired link or a wireless link, such as a Bluetooth connection.

The external device may be a wearable device.

The external device may be arranged to store information based on data received from the wearable neuromodulation device to permit remote monitoring of their condition and/or review of the user's condition by a medical professional, for example, in a telemedicine application.

The external device may be arranged to reprogram the device. For example, the external device may be a computer arranged to send software updates to the device.

The external device may be arranged to receive and execute program instructions from a remote device.

The neuromodulation arrangement may be configured so that data can be transmitted from the neuromodulation device to said external device via a wired link or via a wireless link, such as a Bluetooth® link or via a Body Area Network (BAN).

According to a second aspect of the invention, a method of treating urinary incontinence comprises providing a wearable neuromodulation device for insertion into a pelvic orifice of a human body, the wearable neuromodulation device comprising at least one sensor and means for applying electrical pulses selectively to pudendal nerves through the wall of a rectum or vagina of the human body, using said at least one sensor to detect one or more conditions indicating bladder overactivity and, in response to said detection, using said means for applying electrical stimulation signals to apply a burst of said electrical pulses.

The method may further comprise determining if the frequency of occurrences of said one or more conditions exceeds a predetermined threshold and, in response to a positive determination, applying electrical pulses to stimulate the urethral sphincter for an extended time period.

According to a third aspect of the invention, a method of treating faecal incontinence comprises providing a wearable neuromodulation device for insertion into a pelvic orifice of a human body, the wearable neuromodulation device comprising at least one sensor and means for applying electrical stimulation signals selectively to the pudendal nerves through the wall of a rectum or vagina of the human body, detecting one or more conditions indicating potential faecal leakage and, in response to said detection, applying a burst of said electrical pulses.

The method may further comprise determining if the frequency of occurrences of said one or more conditions exceeds a predetermined threshold and, in response to a positive determination, applying electrical pulses to stimulate the urethral sphincter for an extended time period.

According to a fourth aspect of the invention, a method of treating muscle spasticity comprises providing a wearable neuromodulation device for insertion into a pelvic orifice of a human body, the wearable neuromodulation device comprising at least one sensor and means for applying electrical stimulation signals selectively to stimulate pudendal nerves through a wall of a rectum or vagina of the human body, detecting one or more conditions indicating spasticity and, in response to said detection, applying a burst of said electrical pulses.

According to a fifth aspect of the invention, a method of treating muscle spasm comprises providing a wearable neuromodulation device for insertion into a pelvic orifice of a human body, the wearable neuromodulation device comprising at least one sensor and means for applying electrical stimulation signals selectively to stimulate pudendal nerves through a wall of a rectum or vagina of the human body, detecting one or more conditions indicating a muscle spasm and, in response to said detection, applying a burst of said electrical pulses According to a sixth aspect of the invention, a method of preventing muscle wastage comprises providing a wearable neuromodulation device for insertion into a pelvic orifice of a human body, the wearable neuromodulation device comprising means for applying electrical stimulation signals selectively to stimulate pudendal nerves through the wall of a rectum or vagina of the human body and applying a burst of said electrical pulses.

According to a seventh aspect of the invention, a method of enhancing a guarding reflex comprises providing a wearable neuromodulation device for insertion into a pelvic orifice of a human body, the wearable neuromodulation device comprising at least one sensor and means for applying electrical stimulation signals selectively to pudendal nerves through the wall of a rectum or vagina of the human body in order to stimulate the guarding reflex, detecting one or more conditions indicating a voluntary guarding reflex and, in response to said detection, applying a burst of said electrical pulses.

The method may further comprise reconfiguring the wearable neuromodulation device to reduce the amplitude of the electrical pulses applied in response to future detections.

According to an eighth aspect of the invention, a method of improving bladder capacity comprises providing a wearable neuromodulation device for insertion into a pelvic orifice of a human body, the wearable neuromodulation device comprising at least one sensor and means for applying electrical pulses selectively to pudendal nerves through the wall of a rectum or vagina of the human body to stimulate a urethral sphincter of the human body, using said at least one sensor to detect one or more conditions indicating bladder overactivity and, in response to said detection, using said means for applying electrical stimulation signals to apply a burst of said electrical pulses.

The method may further comprise reconfiguring the wearable neuromodulation device to reduce the amplitude of the electrical pulses applied in response to future detections.

According to a ninth aspect of the invention, a method of improving bowel capacity comprises providing a wearable neuromodulation device for insertion into a pelvic orifice of a human body, the wearable neuromodulation device comprising at least one sensor and means for applying electrical pulses selectively to pudendal nerves through the wall of a rectum or vagina of the human body to stimulate an anal sphincter of the human body, using said at least one sensor to detect one or more conditions indicating rectal overactivity and, in response to said detection, using said means for applying electrical stimulation signals to apply a burst of said electrical pulses.

The method may further comprise reconfiguring the wearable neuromodulation device to reduce the amplitude of the electrical pulses applied in response to future detections.

BREIF DESCRIPTION OF THE DRAWINGS

The embodiments of the invention will now be described with reference to the accompanying drawings, of which:

FIG. 9b is an enlarged view of a portion of the graph of FIG. 9a;

DETAILED DESCRIPTION

Figure 1:
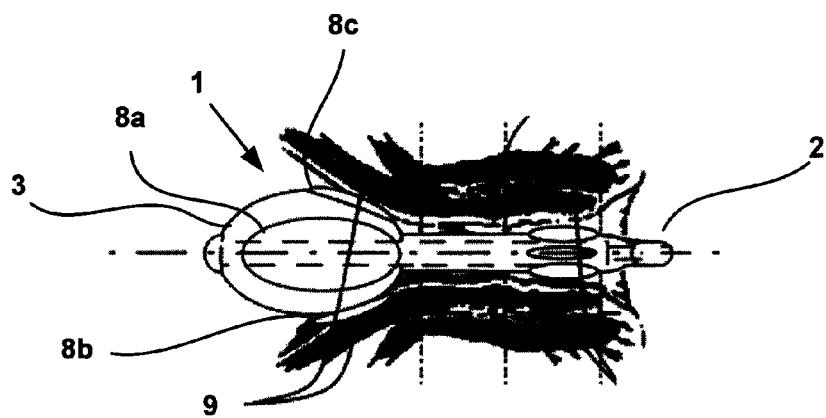
FIG. 1 depicts a device according to an embodiment of the invention when in use.
Figure 2:
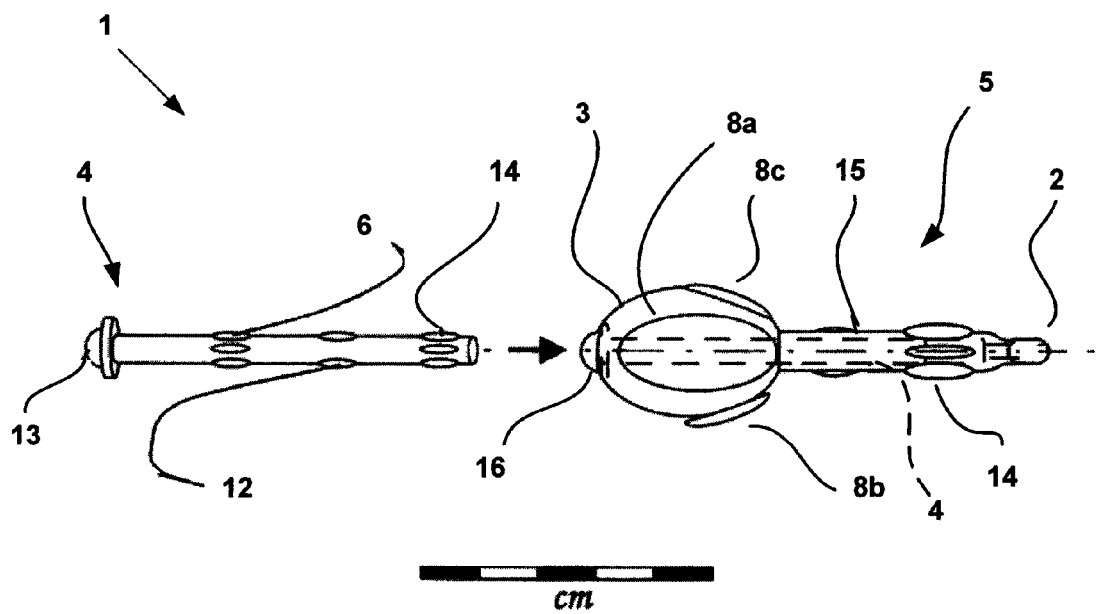
FIG. 2 depicts the device shown in FIG. 1 with its sleeve removed and with its sleeve in place.
Figure 3:
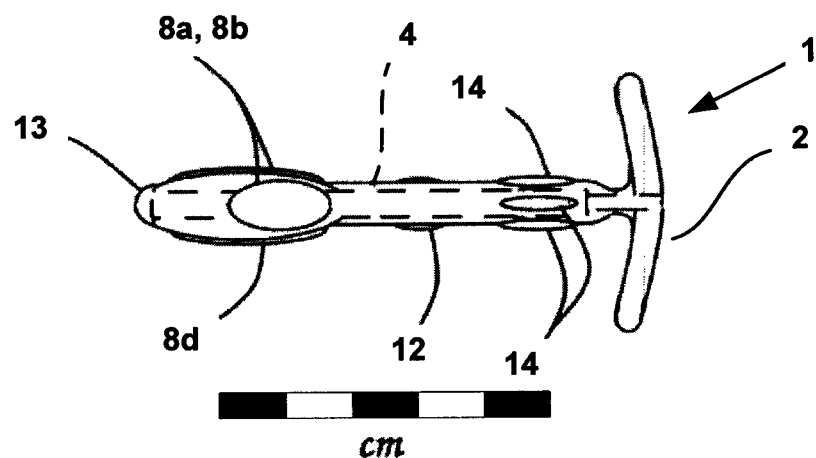
FIG. 3 is a side elevation of the device shown in FIG. 1.

FIG. 1 depicts a device 1 according to an embodiment of the invention when in use. The device 1 is positioned in a pelvic orifice of a patient, such as the anus or vagina. In the example shown in FIG. 1, the device 1 is placed in the anal canal of a patient so that one end, comprising an anchor portion 2, remains outside the body and the a bulb portion 3, at the opposite end, extends into the rectum. The anchor portion 2 and bulb portion 3 and is configured to retain the device 1 in this position. The anchor portion 2 also assists in removal of the device 1, for example, for egestion of the bowel. FIGS. 2 to 5 and 6a are further views of the device 1.

The device 1 comprises an electronic module 4, in which electronic circuitry for controlling the stimulation applied to a patient is enclosed within a hermetic case.

The device 1 also comprises a removable sleeve 5 that fits over the module 4 to provide a watertight seal. In this example, the sleeve 5 is of moulded soft medical grade silicone rubber for biocompatibility with anal canal mucosa. The use of such a soft material can improve comfort for the wearer.

This configuration permits the replacement of the outer sleeve 5. Such replacement may be required following damage or deterioration of the outer sleeve 5, such as discolouration of the outer sleeve 5 as a result of staining by waste products. While such discolouration would not affect the functioning of the device 1, it could potentially discourage a patient from continuing to use the device 1. Therefore, by allowing the patient to remove the outer sleeve 5 and replace it with a new sleeve, patient compliance may be improved.

The module 4 comprises electrical contacts 6. When the sleeve 5 is fitted over the module 4, the contacts 6 mate with, and are thus electrically connected to, contacts 7 of corresponding stimulation electrodes 8a, 8b, 8c, 8d on the sleeve 5.

Figure 4:
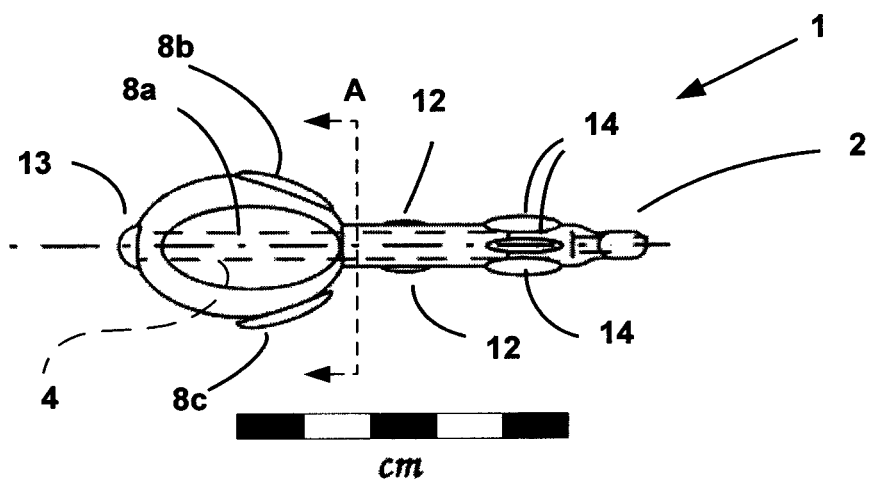
FIG. 4 is a plan view of the device shown in FIG. 1.
Figure 5:
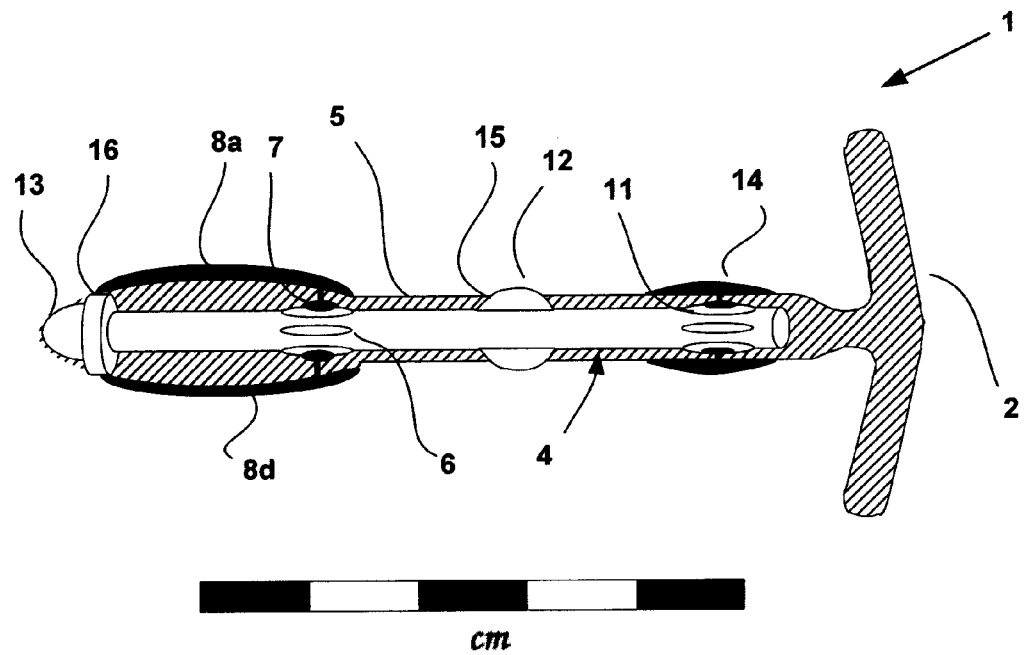
FIG. 5 is a cross-sectional plan view of the device shown in FIG. 1.
Figure 6A:
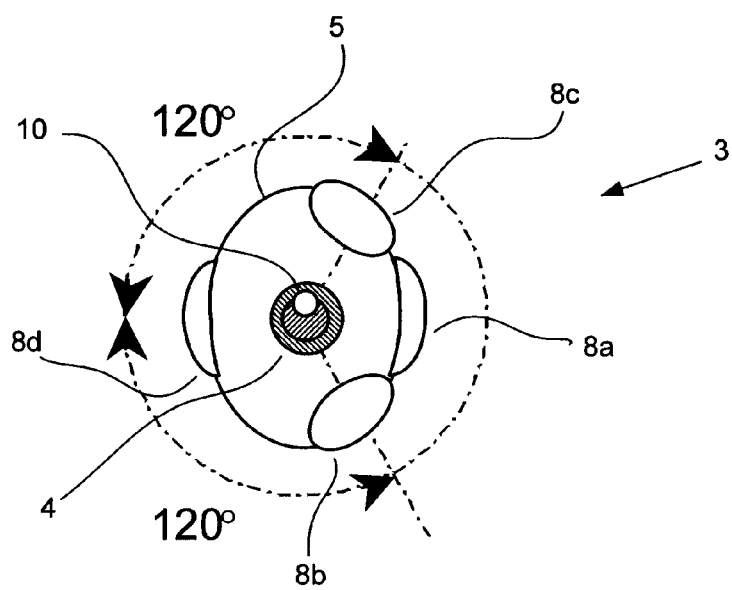
FIG. 6a is a cross sectional view of a bulb portion of the device shown in FIG. 1.

FIG. 6a is a cross-sectional view of the bulb portion 3 of the device 1, when seen from a position along line A in FIG. 4. As shown in FIG. 6a, the stimulation electrodes 8a-8d have a circumferential configuration. The anchor portion 2 and bulb portion 3 of the device are arranged so that, in use, the stimulation electrodes 8-8d are situated in the rectum and are closely apposed to the pudendal sensory and motor nerves 9, as shown in FIG. 1, so that stimulation can be applied thereto. In order to achieve this, the device is configured the anchor portion 2 and the stimulation electrodes 8a-8d are separated by a distance of at least 3 centimetres.

In this particular example, the contacts 6 are tripolar contacts and the stimulation electrodes 8a, 8b, 8c comprise a tripole arrangement including an anode 8a and two cathodes 8b, 8c. The cathodes 8b, 8c are arranged so that they are between 100 degrees and 140 degrees apart, with respect to a longitudinal axis of the device 1. Preferably, the centres of the cathodes 8b, 8c are 120 degrees apart, so that they are closely apposed to the pudendal nerves. Optionally, a second anode 8d may be provided, located at a position substantially opposite to the anode 8a.

The anode 8a and, where provided, second anode 8d have a larger surface area than the cathodes 8b, 8c. Consequently, the electric field in the vicinity of the cathodes 8b, 8c has a higher current density than the electric field in the vicinity of the anode 8a. This causes the stimulation pulses to be focussed in the region of the cathodes 8b, 8c, thereby focussing the stimulation on the parts of the rectal wall that are closest to the pudendal nerves.

The stimulation electrodes 8a-8d are formed of carbon loaded silicone rubber. Carbon loaded silicone rubber is suitable for this application as it is flexible, thereby increasing the comfort of the patient, has a low impedance and is compatible with human mucosa and skin. However, other materials, including platinum wire, platinum coated onto silicone rubber, other noble metals and medical grade stainless steel, could also be used to form the stimulation electrodes 8.

Figure 6B:
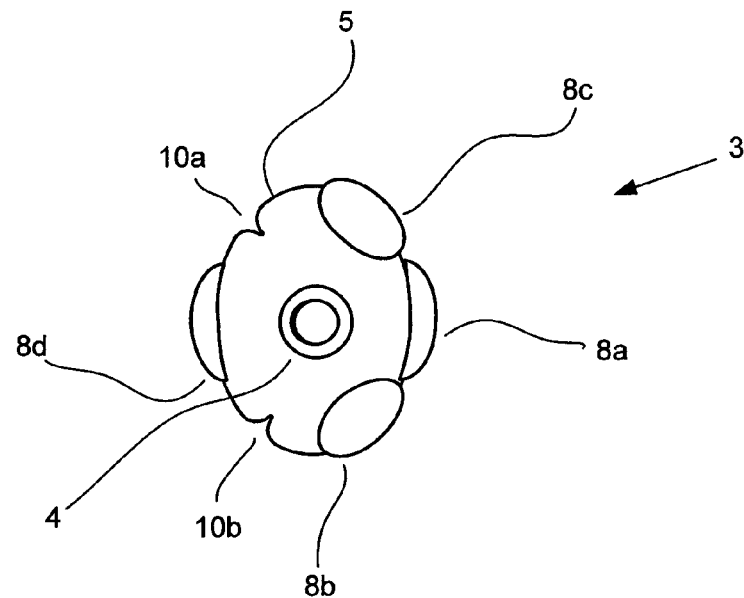
FIG. 6b is a cross sectional view of a bulb portion of a device according to a second embodiment of the invention.

In this particular example, a leakage path is provided, in order to allow passage of intestinal gas. In this particular example, the leakage path is a channel 10 that extends through the sleeve 5 and module 4, as shown in FIG. 6a. However, in other embodiments of the invention, alternative types of leakage path may be provided instead of, or in addition to, channel 10. For example, FIG. 6b is a cross-sectional view of a device according to a second embodiment of the invention, which comprises the same features as the device of FIG. 1, with the exception of the leakage path. In the device of FIG. 6b, the channel 10 is replaced with a plurality of grooves 10a, 10b, provided in the sleeve 5 of the device. Alternatively, the leakage path may be omitted altogether, if not required.

Returning to the first embodiment, shown in FIGS. 2 to 5 and 6a, the device 1 is provided with sensors 11, 12, 13 arranged to monitor the activity of the anal sphincter and/or rectum and detect any inappropriate contraction thereof. In this particular embodiment, two types of sensor are provided.

A sensor for detecting electromyographic (EMG) signals caused by external (striated) anal sphincter electrical activity is provided as follows. The module 4 comprises tripolar contacts 14. Carbon-silicone sensing electrodes 11 having a longitudinal circumferential configuration corresponding to the contacts 14 are provided on the sleeve 5, in a similar manner to that discussed above in relation to the stimulation electrodes 8a-8d and contacts 6. In use, the sensing electrodes 11 are located adjacent to the external anal sphincter.

Secondly, pressure sensors 12, 13 are arranged to detect increased pressure in the anal canal and rectum respectively. The pressure sensors 12, 13 protrude through the case of the electronics module 4 and extend through apertures 15, 16 provided in the sleeve 5.

The electronic module 4 is arranged to control the application of electrical stimulation signals via the stimulation electrodes 8a-8d in accordance with the output of the sensors 11, 12 or 13. For example, where a patient has suffered a spinal cord injury, neurogenic bladder overactivity is manifest as large pressure rises in the bladder, associated with a combination of urethral sphincter co-contraction, known clinically as detrusor sphincter dyssynergia. Dyssynergia is often accompanied by leakage of urine. The urethral sphincter dyssynergic contractions are invariably accompanied by similar activity in the anal sphincter. This activity is detected by the sensors 11, 12.

The device 1 responds to the increased EMG signals and/or pressure by providing appropriate stimulation to the pudendal nerves. This causes immediate reflex suppression of the bladder overactivity, direct motor activation of the sphincters and the prevention of incontinence. In this manner, stimulation is applied only when required by the patient, reducing the likelihood of habituation and reducing the power consumption of the device 1 when compared with the prior continuous stimulation devices discussed above.

Furthermore, the use of conditional stimulation makes the device 1 suitable for patients having at least some volitional control of their sphincters and good "guarding" reflexes. In such patients, conditional neuromodulation may be effected by a combination of reflex activation of the sphincter, in response to stimulation, and voluntary contraction.

Figure 7:
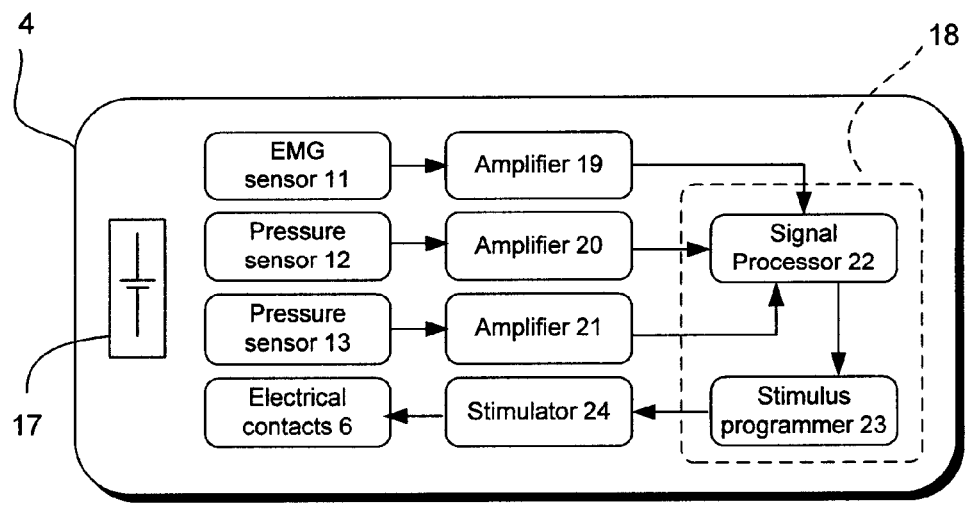
FIG. 7 is a block diagram of an electronic module of the device shown in FIG. 1.

FIG. 7 comprises a block diagram of the module 4. In this particular example, the module 4 is powered by a rechargeable battery 17 and controlled by a microprocessor 18.

The module 4 comprises amplification means 19, 20, 21 for amplifying data signals output by the sensors 11, 12, 13 and a signal processor 22 for determining whether the amplified data signals indicate a condition requiring stimulation and a stimulus programmer 23 configured to generate control signals for controlling the contacts 6 and stimulation electrodes 8a-8d, based on the processed signals, via a stimulator 24. In this particular embodiment, the functions of the signal processor 22 and stimulus programmer 23 are performed by the microprocessor 18.

In the device shown in FIG. 7, the signal processor 22 is arranged to determine whether stimulation is required, based on the data output by the sensors 11, 12, 13. The amplified data signal from the EMG sensor 11, output by the amplifier 19, is integrated and the amplified data signals from the pressure sensors 12, 13, output by amplifiers 20, 21, are filtered and/or smoothed. The signal processor 22 then determines whether any of the data signals, or parameters derived from the data signals, exceed respective predetermined threshold levels. The signal processor 22 generates an output signal only if stimulation is needed. However, in an alternative embodiment, the signal processor 22 may be arranged to generate a signal comprising data that indicates whether or not stimulation is required.

Figure 8:
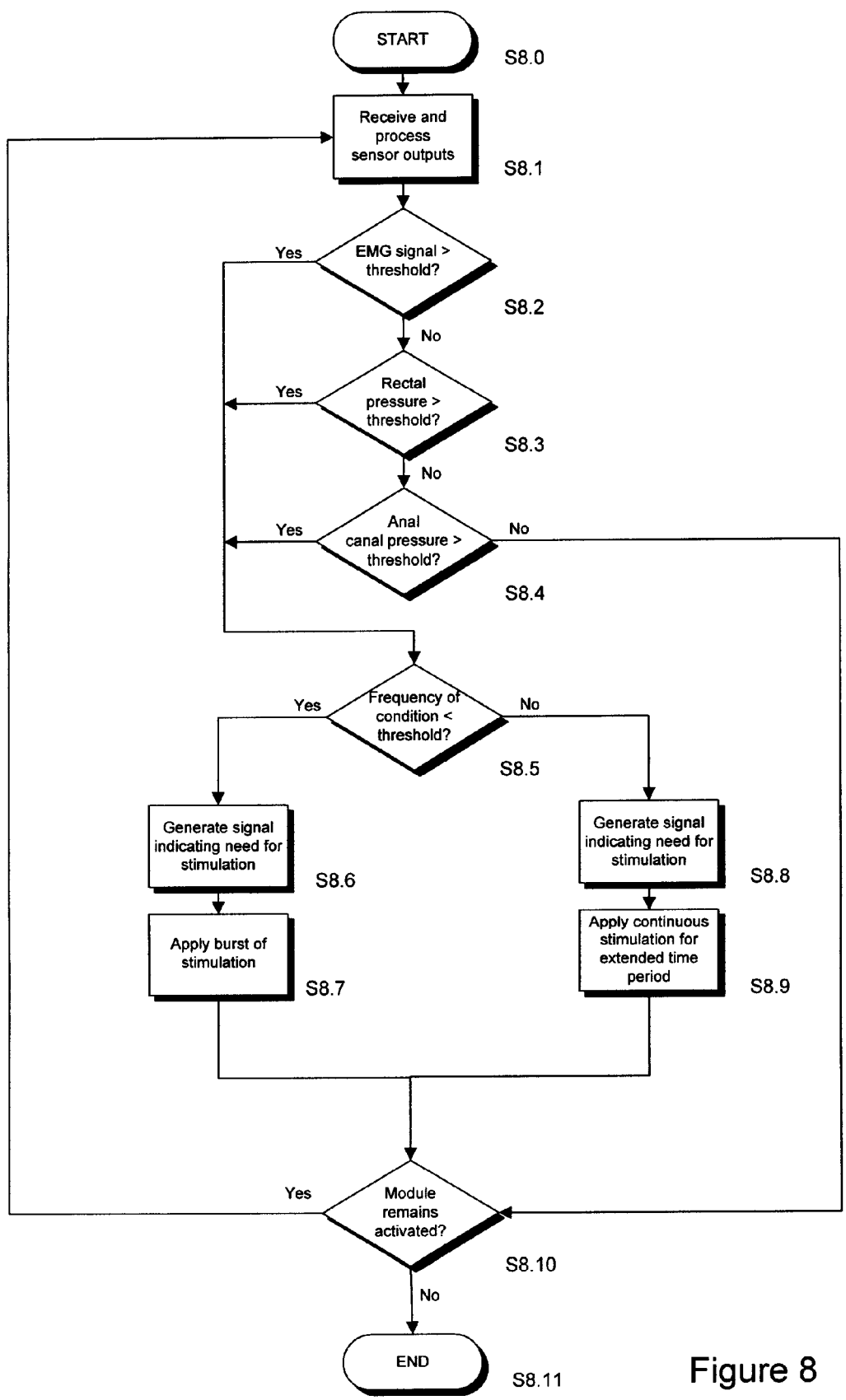
FIG. 8 is a flowchart of a procedure performed by the electronic module shown in FIG. 7.

FIG. 8 is a flowchart of the procedure for selectively applying stimulation using the module 4.

Beginning at step 8.0, the data signals from the sensors 11, 12, 13 are received by the signal processor 22 (step s8.1), following their amplification. The signal processor 22 processes the signals, for example, by integrating the data signal from the EMG sensor 11 and smoothing the data signals from the pressure sensors 12, 13. If required, the signal processor 22 may then derive other parameters from the data signals for use in determining whether or not stimulation is required.

Figure 9A:
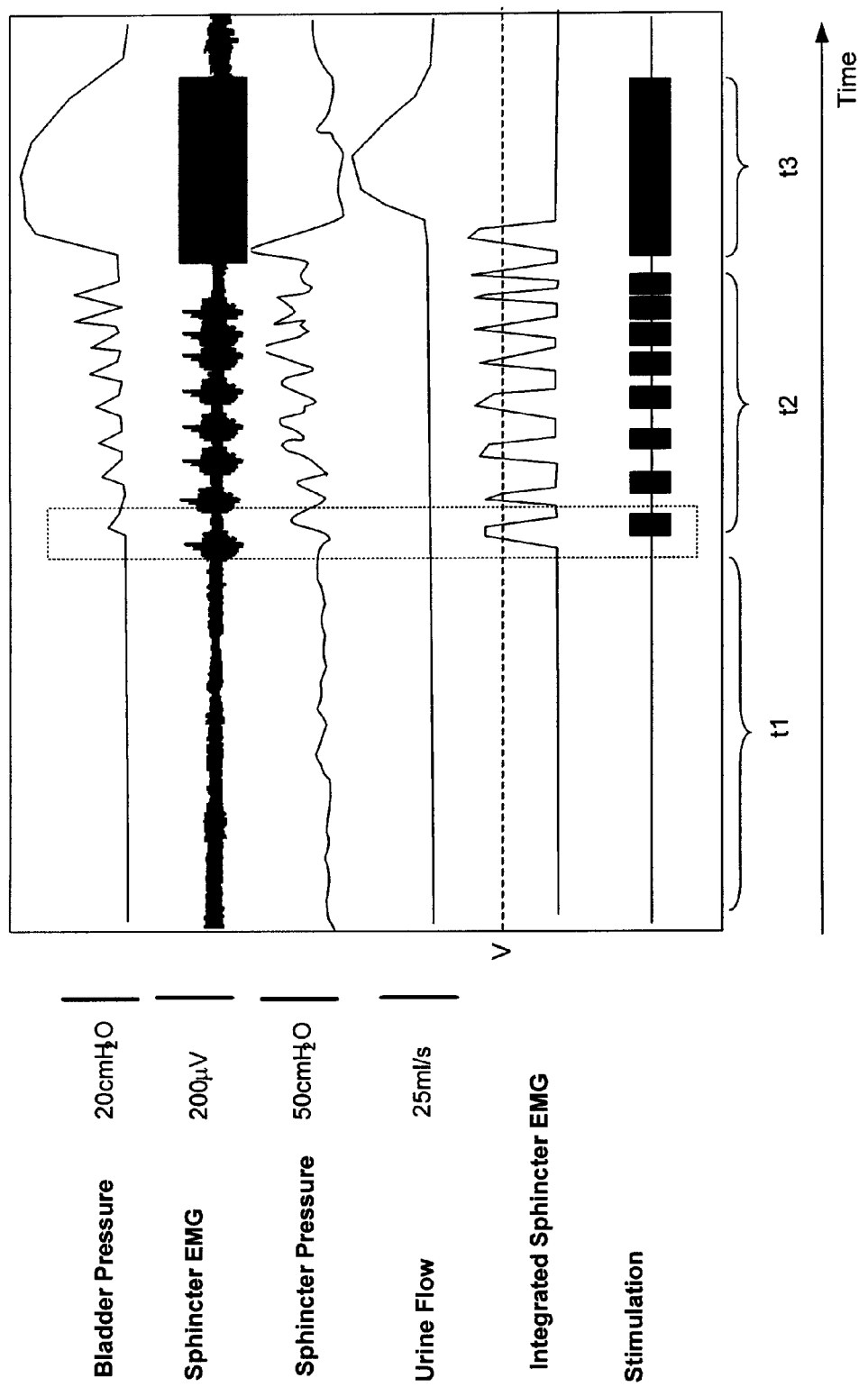
FIG. 9a is a graph showing the change over time of parameters relating to patient condition, sensor signals and applied stimulation for an example stimulation scenario.
Figure 9B:
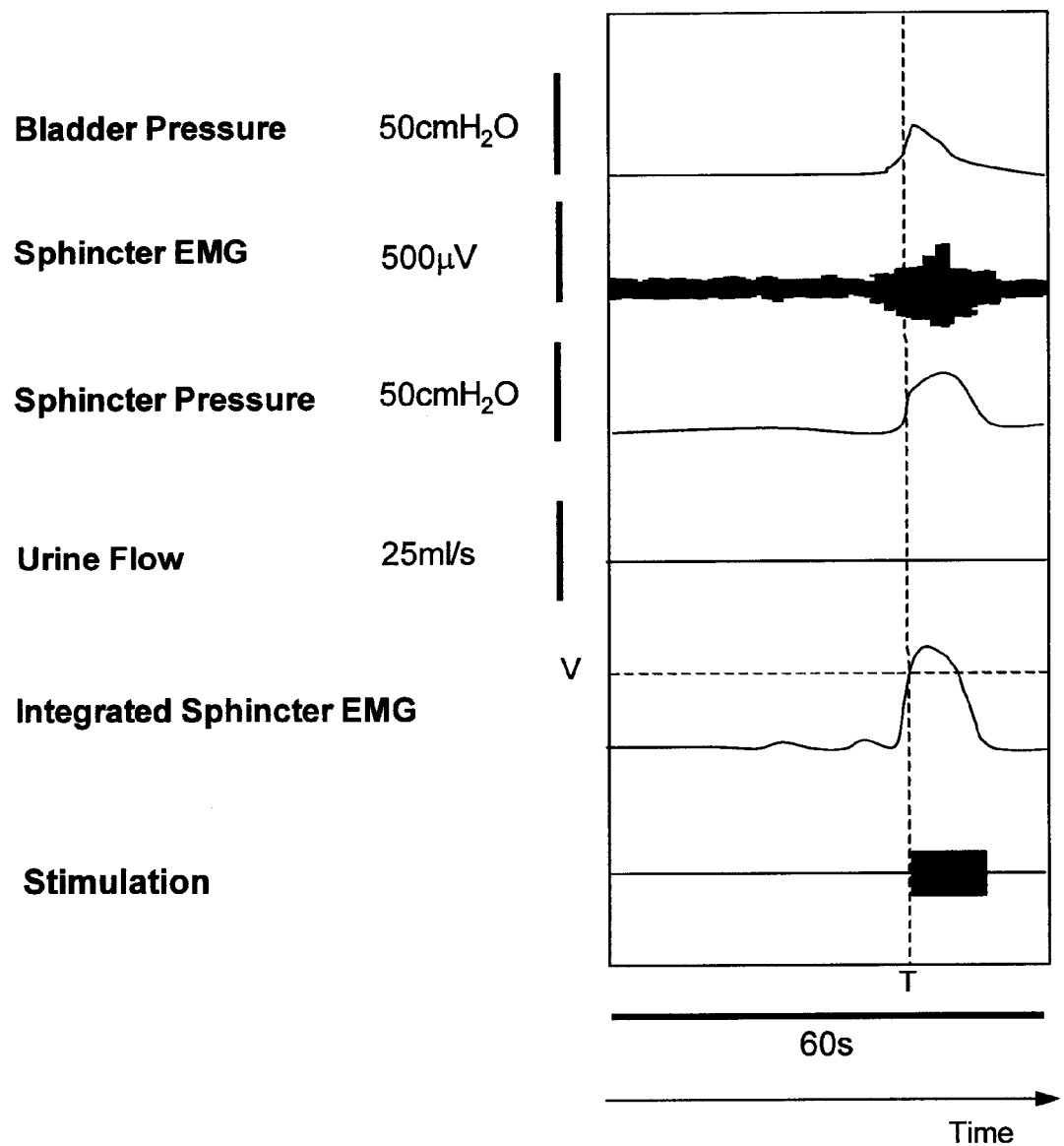

FIG. 9a depicts a sphincter EMG signal, obtained from the EMG sensor 11, and the integrated sphincter EMG signal produced by the signal processor 22. FIG. 9b is an enlargement of the portion of FIG. 9a indicated with dotted lines. Also included in FIGS. 9a and 9b are the bladder pressure and sphincter pressure of the patient. It can be seen that variations in the sphincter EMG signal correspond to changes in the bladder and sphincter pressure and thus provide an indication of a condition requiring stimulation.

The processed signals are then compared with respective predetermined threshold levels. In step s8.2, the integrated EMG signal is compared with a threshold level V. If the EMG signal is less than the threshold V, for example, during time interval t0 in FIG. 9a, the signal processor 22 continues to compare the smoothed data signals from any other sensors provided in the device 1 with their respective thresholds, such as the data signals from the pressure sensors 12, 13, (steps s8.3, s8.4).

If it is determined by the signal processor 22 that the output from the EMG sensor 11 indicates the occurrence of an inappropriate muscle contraction (step s8.2) or that either of the outputs of the pressure sensors 12, 13 indicate that the pressure within the rectum or anal canal of the patient exceeds a respective predetermined threshold (steps s8.3, s8.4 respectively), the signal processor 22 stores an indication that stimulation is required and the time at which the determination was made.

If any of the data signals exceeded their respective thresholds (steps s8.2, 8.3, 8.4), the signal processor 22 determines the frequency with which the data signals have indicated a condition requiring stimulation, based on the stored indication(s). For example, the signal processor 22 may calculate the number of instances in which stimulation has been required in a given time interval and whether said number exceeds a given threshold (step s8.5). Alternatively, the signal processor 22 may calculate the time interval between successive detections of conditions requiring stimulation and determine whether the time interval is less than a predetermined time limit.

Referring again to the example shown in FIG. 9a, as the volume of urine in a patient's bladder rises over time interval t1, the variations in the bladder and sphincter pressures become more marked and the integrated sphincter EMG signal exceeds the EMG threshold V more frequently. Thus, an increased rate of occurrences of conditions requiring stimulation may indicate a need to alter the type or duration of stimulation applied to the patient.

If the frequency does not exceed the relevant threshold (step s8.5), the device 1 generates a relatively short burst of stimulation. Such a scenario is depicted in FIG. 9b, where a condition requiring stimulation is detected at time T0 but no such conditions were detected during the preceding time interval t1. In this case, the signal processor 22 generates a signal indicating that stimulation is required (step s8.6).

The signal output by the signal processor 22 is received by the stimulus programmer 23, which controls the stimulator 24. The stimulator 24 causes a burst of stimulation, of relatively short duration, to be applied to the patient via the contacts 6 and the stimulation electrodes 8a-8d (step s8.7). The burst comprises a series of pulses. The pulses may have a duration between 100 and 300 µs, at a frequency of 10 to 20 pulses per second, with a peak current of 20 mA and a peak voltage up to 20 V, depending on the patient. In this particular example, the pulses have a duration of 250 µs and a frequency of 15 pulses per second while the duration of the burst is approximately 10 seconds.

If, instead, the frequency does exceed the relevant threshold (step s8.5), the device 1 generates continuous stimulation over an extended time period. Referring to the example scenario of FIG. 9a, during the time interval t2 following T0, conditions requiring stimulation are detected with an increasing frequency. At time T1, it is determined that this frequency exceeds the relevant threshold (step s8.5) and continuous stimulation is applied over time interval t3. In this case, the signal processor 22 generates a signal indicating that stimulation is required (step s8.8). The stimulus programmer 23 and stimulator 24 then cause continuous stimulation to be applied to the patient over an extended time period via the contacts 6 and stimulation electrodes 8a-8d (step s8.9). In this particular example, the duration of the extended time period is approximately 80 seconds.

The signals generated by the signal processor 22 at steps s8.6 and s8.8 may differ, according to whether a burst of stimulation or continuous stimulation is required. Alternatively, the signal processor 22 may generate a signal that simply indicates that stimulation is needed. In this case, where continuous stimulation is required, the signal generated by the signal processor 22 would have a longer duration, or be output repeatedly, in order to effect the generation of continuous stimulation.

Following the application of stimulation (step s8.7 or s8.9), or if it is determined at steps s8.2, s8.3 and s8.4 that stimulation is not required, the module 4 remains activated (step s8.10) and continues monitoring the output from the sensors 11, 12, 13 (steps s8.1 to s8.4) and applying stimulation as required (steps s8.5 to s8.9). If the module 4 is deactivated (step s8.10), the procedure ends (step s8.11).

The device 1 is thus a self-contained, autonomous neuromodulation device.

Figure 10:
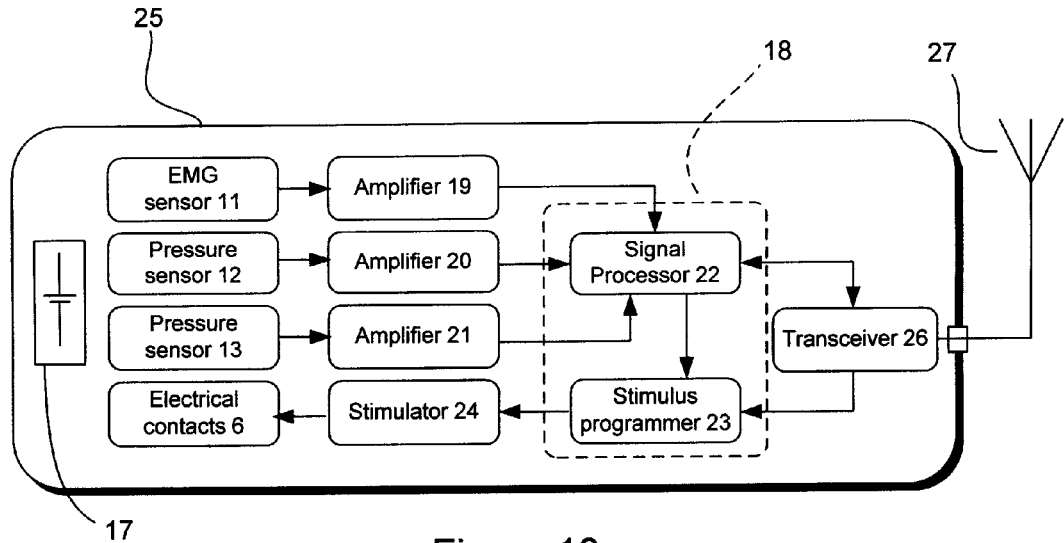
FIG. 10 is a block diagram of an electronic module according to a third embodiment of the invention.

In another embodiment of the invention, the device 1 comprises a module 25, shown in FIG. 10, that is arranged to communicate with an external device.

The module 25 of FIG. 10 differs from the module 4 of FIG. 7 by including a transceiver 26 and antenna 27 for transmitting data to and receiving data from one or more other devices.

Figure 11:
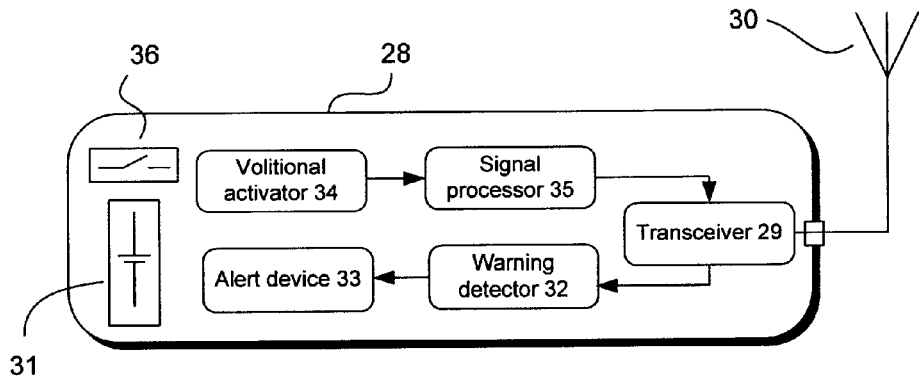
FIG. 11 is a block diagram of an external device for use with the electronic module of FIG. 10.

The one or more other devices may include an external device 28, shown in FIG. 11, for alerting and/or conveying commands from of the patient using the device 1.

The external device 28 is provided with a transceiver 29 and antenna 30 for transmitting and receiving data from the module 25 and powered by a rechargeable battery 31. A sensory warning detector 32 is arranged to respond to the reception of the signal from the signal processor 22 of the module 25 by activating an alert device 33, to inform the patient of their condition.

In this particular embodiment, the external device 28 is a wearable device, that may be clipped onto clothing, worn on a belt, kept in a pocket or similar, and the alert device 33 comprises vibrating means so that the alert is discreet. However, other alert devices can be provided in addition to, or instead of, the vibrating means. For example, a visual indication, such as a light, or audible indication, such as a buzzer, may be provided.

The alert facility is particularly advantageous where the patient has no sensation in the lower part of their body. For example, if the patient has suffered a spinal cord injury, they may not be able to sense the nerve signals that would indicate the need to contract their sphincter muscles to prevent urine or faecal leakage. If the module 25 is applying stimulation at frequent intervals, this could indicate a need for continuous stimulation and an imminent need to empty the bladder or bowel.

The external device 28 may also include a personal volitional activator 34. Thus, while the module 25 is self-contained and autonomous, a patient can use the personal volitional activator 34 to override the signal generated by the signal processor 22. This facility permits the patient to control the device 1 in order to promote contraction of the sphincter, using relative low frequency stimulation as described above, and/or emptying of the bladder or bowel, using relatively high frequency stimulation. The personal volitional activator 34 may be in the form of a switch, button, dial or the like.

A signal processor 35 is provided for detecting activation of the personal volitional activator 34 and generating a control signal based thereon. The control signal can indicate the type of stimulation required, for example, a burst or continuous stimulation, high or low frequency, and so on. The control signal is transmitted to the device 25 via the transceiver 29 and antenna 30 and received and acted on by the stimulus programmer 23 of the module 25. In this manner, the device 1 can provide neuromodulation on demand.

This arrangement is particularly useful where the patient has suffered a spinal cord injury. In such a case, neurogenic bladder overactivity is manifest as large pressure rises in the bladder, associated with a combination of urethral sphincter co-contraction, known clinically as detrusor sphincter dyssynergia. Dyssynergia is often accompanied by leakage of urine. The urethral sphincter dyssynergic contractions are invariably accompanied by similar activity in the anal sphincter. This activity is detected by the sensors 11, 12, 13 and the device 1 responds by applying appropriate stimulation, as directed by the control signals from the signal processor 22. The effect of this conditional stimulation is to enlarge the bladder capacity and, as it does so, the episodes of conditionally suppressed overactivity and dyssynergia become more frequent until suppression becomes ineffective and reflex voiding ensues. The provision of an alert allows the patient to be forewarned of this event by the increased frequency of the application of the stimulation. Thus, the patient can prepare for voiding of the bladder. Such voiding can be promoted by using the personal volitional activator 34 to cause the device 1 to apply higher frequency stimulation, for example, with a frequency of 40 pulses per second, of the pudendal nerves.

The external device 28 also comprises an on/off switch 36, to allow the patient to deactivate the device 1 and/or external device 28 when not in use.

Figure 12:
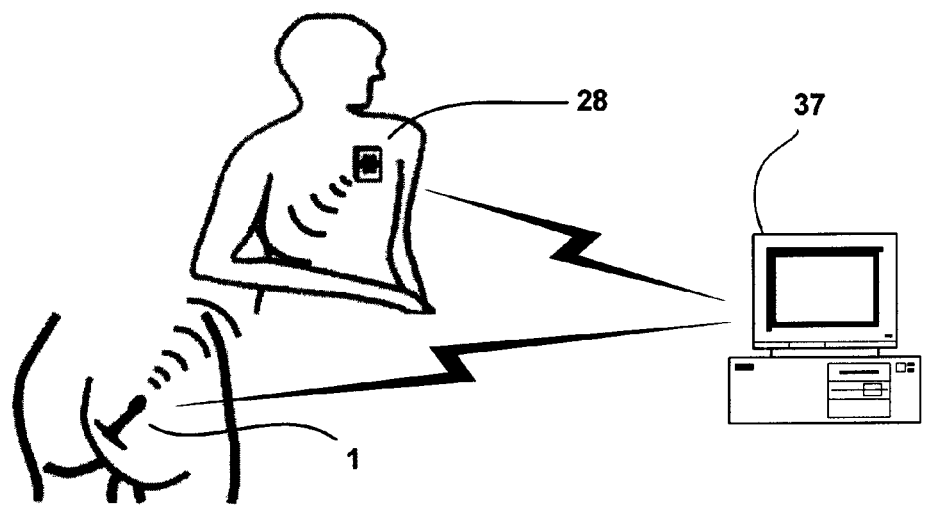
FIG. 12 depicts a neuromodulation arrangement according to an embodiment of the invention.

Referring to FIG. 12, the one or more other devices may include a remote device, such as a computer 37, in addition to, or instead of, the external device 28. The computer 37 may act as an independent monitoring unit, allowing the patient's condition to be monitored remotely, and/or as a data logger compiling and storing records relating the patient's condition for medical functional and operational diagnostic purposes. Such data could be transmitted continuously, periodically or in response to a determination by the signal processor 22 that stimulation is required.

Although the external device 28 of FIG. 11 comprises a sensory warning detector 32 and a sensory actuator 33, it is not essential to provide such means for alerting the patient. Similarly, an alternative external device can be configured without a personal volitional activator 34 and signal processor 35. Where either, or both, of these features are provided, the alert signal and/or control signal generated by the signal processor may also be transmitted to computer 37, if required.

The external device 28 of FIG. 11 is powered by a rechargeable battery 31. However, in an alternative embodiment, the external device may instead be powered by a replaceable, non-rechargeable battery.

Where provided, the computer 37 may transmit reprogramming instructions to the signal processor 22 and/or stimulus programmer 23 of device 1 and, if required, to the signal processor 35 of the external device 28 in order to update or adapt their operation. For example, in a telemedicine arrangement, the computer 37 can be used to reprogram the device 1 to alter the parameters of the stimulation, such as the amplitude, duration and frequency of the pulses, and/or the thresholds used to evaluate the need for stimulation from the outputs of the sensors 11, 12, 13 and the frequency of conditions requiring stimulation (steps s8.2 to s8.5). Such reprogramming may be required where the patient has a guarding reflex or response that is improved through their use of the device 1.

In the arrangement shown in FIG. 12, the data signals and control signals are transmitted between the device 1 and external device 28 via a wireless link. The wireless link may be a short range radio communication link. If the wireless communication link uses a protocol such as Bluetooth®, the device 1 and external device 28 will recognise each other when activated and automatically configure the link. If required, the device 1 and external device 28 can be configured to run authentication procedures when configuring the communication link, in order to ensure that the device 1 does not transmit and receive signals from other external devices 28 within its communication range. Alternatively, the link between the device 1 and external device 28 may be provided via a Body Area Network (BAN), in which the body of the patient provides the medium through which the data signals and control signals are transmitted.

Figure 14:
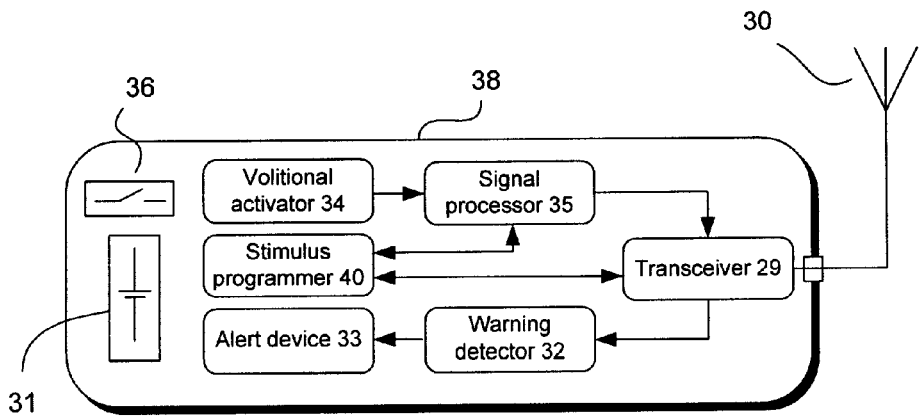
FIG. 14 is a block diagram of an external device for use in the neuromodulation arrangement of FIG. 13.
Figure 13:
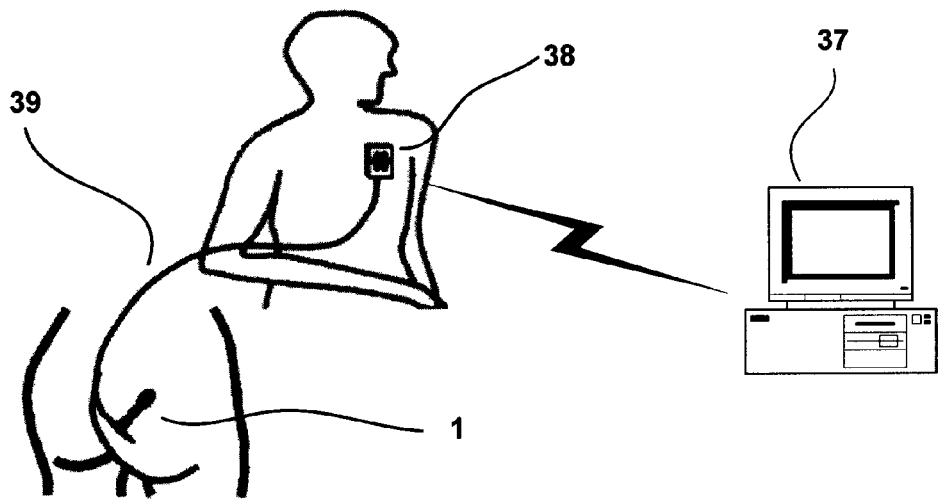
FIG. 13 depicts a neuromodulation arrangement according to another embodiment of the invention.

While the device 1 and external device 28 shown in FIG. 12 communicate via a wireless communication link, in an another embodiment of the invention, shown in FIG. 13, the communication link between the device 1 and an external device 38 is provided using a wired connection, such as a cable 39, as shown in FIG. 13. The use of such a cable 39 may be less comfortable, and less convenient, for the patient but may be of particular use in a home environment. In such an embodiment, the external device 38 may still be provided with an antenna 30 to permit transmission of data signals, control signals, and so on to a computer 37 or other remote device.

Where the device 1 and external device 38 communicate with each other via a wired connection 39, some of the functionality of the module 25 may be transferred to the external device 38. For example, FIG. 14 depicts an external device 38 comprising a stimulus programmer 40. The stimulus programmer 40 performs the same functions as the stimulus programmer 23 of the module 25 of FIG. 10. Therefore, the stimulus programmer 23 can be omitted from the module 25. When the signal processor 22 of the module 25 determines that stimulation is required, it generates a signal that is transmitted to the external device 38. The stimulus programmer 40 then generates the control signals for controlling the stimulator 24 in the device 1 in the manner described above.

Figure 15:
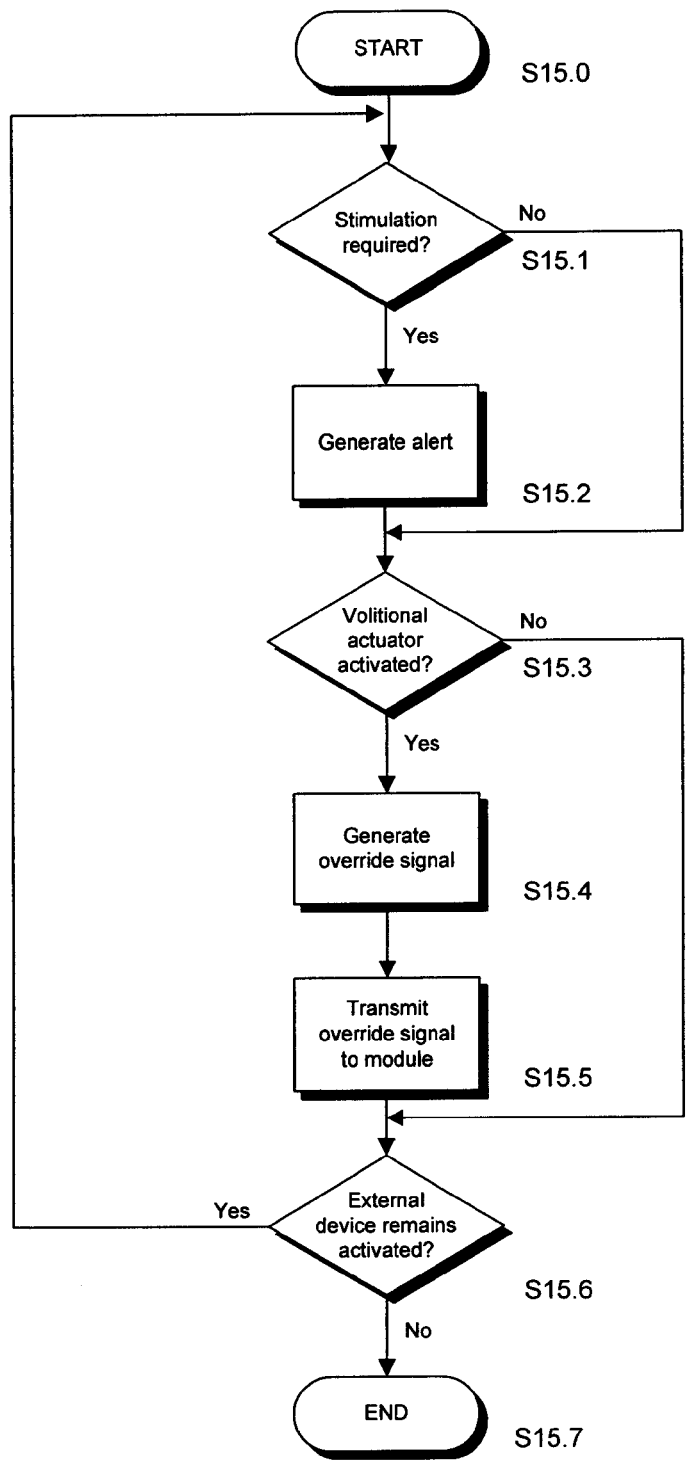
FIG. 15 is a flowchart of a procedure for performed by a neuromodulation arrangement comprising the electronic module of FIG. 9 and the external device of FIG. 11.

FIG. 15 is a flowchart of the general procedure performed by the external device 28 of FIG. 11.

Beginning at step s15.0, the signal processor determines whether a signal indicating a need for stimulation has been received from the device 1 (step 15.1). If so, an alert is generated by the sensory warning detector 32 and sensory warning actuator 33 (step s15.2).

The external device 28 then determines whether the personal volitional activator 34 has been activated by the patient (step s15.3). If so, the signal processor 35 generates an override signal (step s15.4) according to the stimulation requested by the patient. For example, the patient may request continuous stimulation, in order to avoid urine leakage, or high frequency stimulation in order to promote voiding of the bladder.

The override signal is then transmitted to the device 1 (step s15.5) and directed to the stimulus programmer 23. The requested stimulation is then applied by the stimulator 24 via the electrical contacts 6 and stimulation electrodes 8*a*-8*d*.

If the device 1 has not been deactivated (step s15.6), via the on/off switch 36, the external device 28 returns to monitoring signals received from the device 1 (step s15.1), generating alerts (step s15.2) and responding to activation of the personal volitional actuator 34 (steps s15.3 to s15.5) as required.

If the device 1 has been deactivated (step s15.6), the procedure ends (step s15.7).

In the device 1 described above, the distance between the stimulation electrodes 8*a*-8*d* and the anchor portion 2 is approximately 3 centimetres. However, in other embodiments of the invention, this distance may be adjusted, for use in patients with anal canals of varying length.

Figure 16:
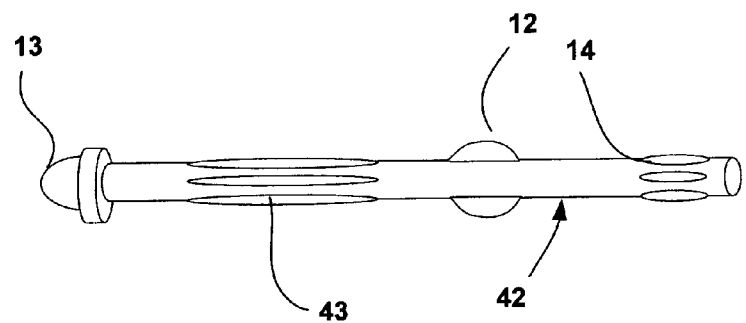
FIG. 16 depicts a module of an adjustable device according to a further embodiment of the invention.
Figure 17:
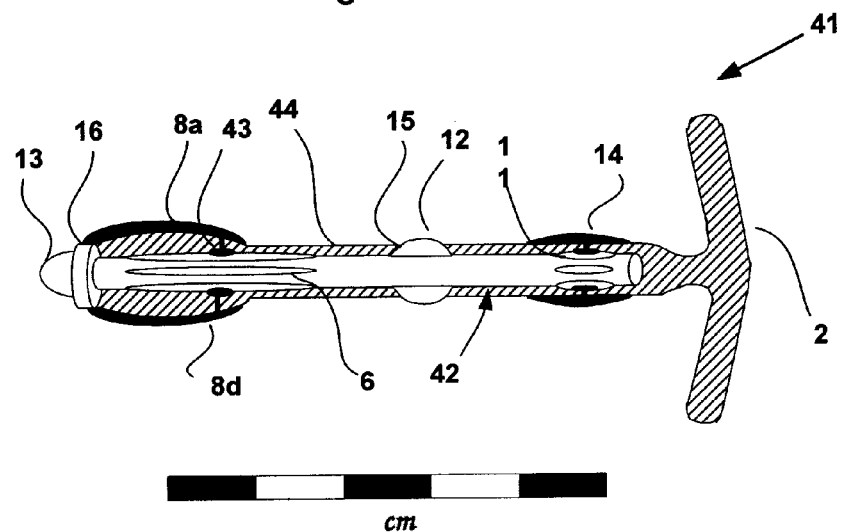
FIG. 17 depicts a device comprising the module of FIG. 16.

FIGS. 16 and 17 depict a device 41 according to another embodiment of the invention. The device 41 comprises an alternative module 42, in which the contacts 43 are elongated along the longitudinal axis of the device. The module 42 can thus accommodate a variety of removable sleeves 44, in which the bulb portion 3, stimulation electrodes 8*a*-8*d* and contacts 7 are at different locations along their respective longitudinal axes. If the anal canal of a patient is relatively long, a sleeve 44 having a relatively short bulb portion 3 can be used. When such a sleeve is 44 placed over the module 42, the distance between the stimulation electrodes 8*a*-8*d* and the anchor portion 2 is relatively long. Due to their elongated shape, the contacts 43 of the module 42 can mate with the contacts 7 of the stimulation electrodes 8*a*-8*d* at a number of positions along the length of the module 42 and can thus accommodate sleeves in which the stimulation electrodes 8*a*-8*d* are positioned at various locations along the length of the module 42.

Figure 18:
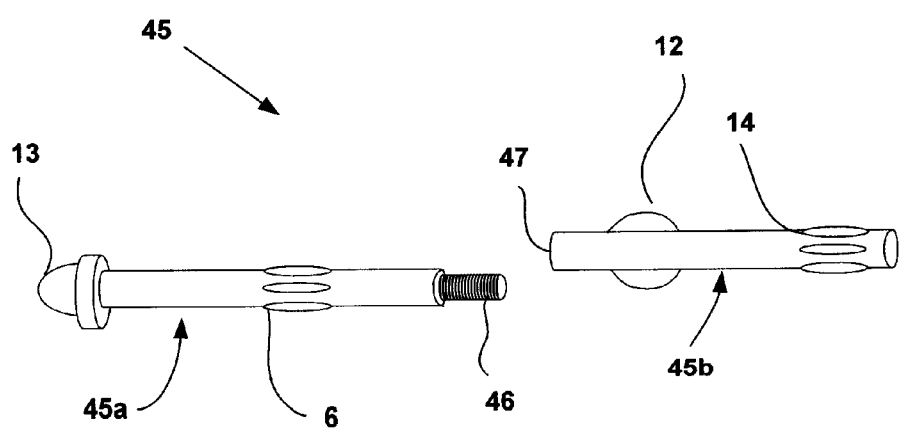
FIG. 18 depicts a module of an adjustable devices according to a yet further embodiment of the invention.

FIG. 18 depicts an alternative module 45 for use in a device according to a yet further embodiment of the invention, which comprises two sections 45*a*, 45*b* that can be connected together using a screw mechanism 46, 47. In this case, different sleeves 5, 44 can be accommodated by adjusting the length of the module 45 using the screw mechanism 46, 47 to adjust the position of the contacts 6 so that they mate with the contacts 7, 43 of the desired sleeve 5, 44.

While the above described device 1 is configured to apply electrical stimulation signals to the pudendal nerves through a wall of the rectum, a similar device may be used to apply such signals to the pudendal nerves through the wall of a vagina.

The use of the device 1 to control urinary incontinence has been described hereinabove. However, the device 1 may be configured for use in treating other conditions as follows.

The device 1 could be used to selectively stimulate the urethral sphincter and/or anal sphincter, in response to detected overactivity of the bladder or bowel, using the same methods described above, in order improve bladder and bowel capacity respectively. Additionally, or alternatively, the device 1 can be used to control faecal incontinence, by causing the anal sphincter to remain contracted to prevent leakage and/or relaxing the rectum to reduce the patient's urge to empty their bowel and to improve bowel capacity. The amplitude of the pulses used to stimulate and drive the anal sphincter may be somewhat higher than those used to control urinary incontinence.

Other conditions that may be treated using the device 1 include spasticity of the lower limbs.

The device 1 may be used to apply stimulation to the gluteal muscles in order to improve tissue viability in the buttocks, to alleviate or avoid pressure sores. While the improvement of the guarding reflex of a patient was mentioned above, the device 1 could also be used to enhance or reprogram conditioning pathways and muscle use. For example, the device 1 could be used to condition the pelvic floor muscle of a patient.

The above described embodiments provides examples of devices 1 according to the invention. While the above devices 1 comprise an electronics module 4 and a removable outer sleeve 5, in other embodiments of the invention, a unitary device may be provided. Such a unitary device may be formed from soft or spongy medical grade silicone rubber for reasons of biocompatibility.

Furthermore, while in the above described embodiments, the devices 1 include three sensors 11, 12, 13, in other embodiments, one or more of these sensors may be omitted. Where provided, the pressure sensors 12, 13 may be arranged to distinguish between pressures exerted by gases, liquids and solids so that appropriate stimulation can be applied to the patient.

The invention claimed is:

1. A wearable neuromodulation device, configured to be insertable into a rectum of a human body, comprising:
a plurality of pudendal nerve stimulation electrodes configured to apply focussed electrical stimulation signals to pudendal nerves through a wall of the rectum;
at least one sensor configured to detect one or more conditions within said human body that indicate a requirement for stimulation;
means for applying an electrical signal to said electrodes selectively, in response to a determination that said stimulation is required based on a detection of said one or more conditions;
a control module configured to control the plurality of pudendal nerve stimulation electrodes, the at least one sensor and the means for applying an electrical signal;
an anchor formation configured to limit the insertion of the wearable neuromodulation device into the rectum and to facilitate removal of the wearable neuromodulation device therefrom; and
a bulbous formation configured to retain said plurality of pudendal nerve stimulation electrodes in the rectum and to maintain the orientation of said plurality of pudendal nerve stimulation electrodes, wherein the plurality of pudendal nerve stimulation electrodes are situated on a surface of the bulbous formation;
wherein the anchor formation and the bulbous formation situate the plurality of pudendal nerve stimulation electrodes apposed to the pudendal nerves of the human body when the wearable neuromodulation device is inserted into the rectum; and
wherein said plurality of pudendal nerve stimulation electrodes, said at least one sensor and said control module are integral with the device that, in use, is inserted into the rectum.

2. A wearable neuromodulation device according to claim 1, comprising:
a module comprising a plurality of electrical contacts; and
a removable outer sleeve, said plurality of pudendal nerve stimulation electrodes being located on said sleeve; wherein:
the sleeve is configured so that when the sleeve is positioned over said module, the plurality of pudendal nerve stimulation electrodes are connected to corresponding ones of said plurality of electrical contacts; and
said means for applying an electrical signal is arranged to apply the electrical signal via said plurality of electrical contacts.

3. A wearable neuromodulation device according to claim 1 wherein said plurality of pudendal nerve stimulation electrodes comprises a tripole arrangement.

4. A wearable neuromodulation device according to claim 3, wherein said tripole arrangement is an unbalanced tripole arrangement, wherein a first electrode of said plurality of pudendal nerve stimulation electrodes is larger than, and is of opposite charge to, a second electrode and a third electrode of said plurality of pudendal nerve stimulation electrodes.

5. A wearable neuromodulation device according to claim 4, wherein said second electrode and said third electrode are positioned with an angle of 100 to 140 degrees therebetween, with respect to a longitudinal axis of the device, and said first electrode is positioned between said second electrode and said third electrode, within said angle.

6. A wearable neuromodulation device according to claim 1, wherein the anchor formation and the bulbous formation are configured to retain said plurality of pudendal nerve stimulation electrodes at a distance of at least 3 centimetres from the external meatus of the anal canal.

7. A wearable neuromodulation device according to claim 1, wherein the distance between the anchor formation and the bulbous formation is adjustable.

8. A wearable neuromodulation device according to claim 2, wherein each of said plurality of electrical contacts are elongated along a longitudinal axis of the device.

9. A wearable neuromodulation device according to claim 1, wherein said at least one sensor comprises a pressure sensor for detecting pressure in the vicinity of the wearable neuromodulation device and said determination ascertains whether the detected pressure exceeds a predetermined threshold.

10. A wearable neuromodulation device according to claim 1, wherein said at least one sensor comprises a sensor for detecting electromyographic signals in a sphincter muscle and said determination ascertains whether the electromyographic signals indicate inappropriate muscle activity.

11. A wearable neuromodulation device according to claim 1, comprising means for determining whether a frequency of detections of one or more conditions requiring stimulation exceeds a predetermined threshold and, in response to a positive determination, to apply continuous stimulation for an extended time period.

12. A wearable neuromodulation device according to claim 1, comprising means for receiving from a remote device program instructions to be executed by said means for applying electrical stimulation signals.

13. A wearable neuromodulation device according to claim 1, wherein said plurality of pudendal nerve stimulation electrodes comprise carbon loaded silicone rubber.

14. A wearable neuromodulation device according to claim 1, comprising:
a transmitter configured to transmit data relating to an output of said at least one sensor to an external device.

15. A neuromodulation arrangement comprising:
a wearable neuromodulation device according to claim 14; and
said external device, arranged to receive data from said wearable neuromodulation device.

16. A neuromodulation arrangement according to claim 15, wherein said external device is arranged to generate an alert in response to data transmitted from the neuromodulation device.

17. A neuromodulation arrangement according to claim 16, wherein said external device comprises a vibration means arranged to provide a vibrating alert.

18. A neuromodulation arrangement according to claim 16, wherein said external device comprises a visual indicator arranged to provide a visual alert.

19. A neuromodulation arrangement according to claim 16, wherein said external device comprises audio output means arranged to provide an audible alert.

20. A neuromodulation arrangement according to claim 15, wherein said external device comprises control means arranged to control the application of electrical stimulation signals by said wearable neuromodulation device.

21. A neuromodulation arrangement according to claim 15, wherein said external device is a wearable device.

22. A neuromodulation arrangement according to claim 15, wherein said external device is arranged to store information based on data received from the wearable neuromodulation device.

23. A neuromodulation arrangement according to claim 15, wherein said external device is arranged to receive and execute program instructions from a remote device.

24. A neuromodulation arrangement according to claim 15, configured to transmit data from the neuromodulation device to said external device via a wired link.

25. A neuromodulation arrangement according to claim 15, configured to transmit data from the wearable neuromodulation device to said external device via a wireless link.

26. A neuromodulation arrangement according to claim 25, wherein said wireless link is a Bluetooth($^{RTM}$) link.

27. A neuromodulation arrangement according to claim 25, wherein said wireless link is part of a Body Area Network.

* * * * *

UNITED STATES PATENT AND TRADEMARK OFFICE
CERTIFICATE OF CORRECTION

PATENT NO. : 8,644,938 B2  Page 1 of 1
APPLICATION NO. : 12/281691
DATED : February 4, 2014
INVENTOR(S) : Michael Craggs It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1285 days.

Signed and Sealed this
Twenty-ninth Day of September, 2015

Michelle K. Lee
*Director of the United States Patent and Trademark Office*